United States Patent
Buettiker et al.

(10) Patent No.: US 10,799,063 B2
(45) Date of Patent: Oct. 13, 2020

(54) METHOD FOR CLEANING AND/OR DISINFECTING A MILK-CARRYING SYSTEM OF A COFFEE MACHINE, AND COFFEE MACHINE

(71) Applicant: JURA Elektroapparate AG, Niederbuchsiten (CH)

(72) Inventors: Philipp Buettiker, Oberbuchsiten (CH); Pascal Ruetti, Neuendorf (CH)

(73) Assignee: JURA Elektroapparate AG, Niederbuchsiten (CH)

( * ) Notice: Subject to any disclaimer, the term of this patent is extended or adjusted under 35 U.S.C. 154(b) by 0 days.

(21) Appl. No.: 15/124,912

(22) PCT Filed: Mar. 12, 2015

(86) PCT No.: PCT/CH2015/000039
§ 371 (c)(1),
(2) Date: Sep. 9, 2016

(87) PCT Pub. No.: WO2015/135085
PCT Pub. Date: Sep. 17, 2015

(65) Prior Publication Data
US 2017/0013996 A1     Jan. 19, 2017

(30) Foreign Application Priority Data
Mar. 13, 2014   (EP) ..................................... 14405023

(51) Int. Cl.
*A47J 31/60*       (2006.01)
*A61L 2/18*        (2006.01)
(Continued)

(52) U.S. Cl.
CPC ............... *A47J 31/60* (2013.01); *A61L 2/18* (2013.01); *A61L 2/20* (2013.01); *B08B 9/0325* (2013.01);
(Continued)

(58) Field of Classification Search
None
See application file for complete search history.

(56) References Cited

U.S. PATENT DOCUMENTS 7,707,927 B2 *  5/2010  Boussemart .......... A47J 31/061
                                                      99/275
9,211,032 B2    12/2015  Larson et al.
(Continued)

FOREIGN PATENT DOCUMENTS

DE    10 2004 010 452 A1    9/2004
DE    20 2010 010 509 U1   10/2011
(Continued)

OTHER PUBLICATIONS

International Search Report of PCT/CH2015/000039, dated Jun. 19, 2015.

*Primary Examiner* — Mikhail Kornakov
*Assistant Examiner* — Ryan L. Coleman
(74) *Attorney, Agent, or Firm* — Collard & Roe, P.C.

(57) ABSTRACT

A method for cleaning and/or disinfecting a milk-carrying system of a coffee machine for producing coffee mix drinks, and a coffee machine for carrying out the method has the aim of allowing the entire milk-carrying system to be cleaned, completely and in a way that can be easily automated. The milk delivery line is separated from the milk container, for carrying out the cleaning Process, and is connected to a first container, and a second container is arranged under a milk outlet of a milk preparation device of the milk-carrying system. Fluid is then delivered to fluid inlet in order to convey the active cleaning and/or disinfecting substance through the milk delivery line and a milk outlet into the second container. Thereafter, water is conveyed to the air inlet and the fluid inlet is closed, in order thereby to flush the milk-carrying system.

13 Claims, 4 Drawing Sheets

(51) Int. Cl.
 *A61L 2/20* (2006.01)
 *B08B 9/032* (2006.01)
(52) U.S. Cl.
 CPC .......... *B08B 9/0326* (2013.01); *B08B 9/0328* (2013.01); *A61L 2202/17* (2013.01)

(56) References Cited

U.S. PATENT DOCUMENTS

| | | | | |
|---|---|---|---|---|
| 2004/0009281 | A1* | 1/2004 | Green | A47J 31/4485 426/590 |
| 2008/0163896 | A1* | 7/2008 | Ioannone | A47J 31/4485 134/18 |
| 2011/0005407 | A1 | 1/2011 | Reyhanloo | |
| 2011/0017074 | A1 | 1/2011 | Goeltenboth | |

FOREIGN PATENT DOCUMENTS

| | | |
|---|---|---|
| EP | 1 656 863 A1 | 5/2006 |
| EP | 1 872 698 B1 | 3/2010 |
| EP | 2 277 419 A1 | 1/2011 |
| EP | 2 363 051 A1 | 9/2011 |
| WO | 2011/105942 A1 | 9/2011 |

\* cited by examiner

METHOD FOR CLEANING AND/OR DISINFECTING A MILK-CARRYING SYSTEM OF A COFFEE MACHINE, AND COFFEE MACHINE

CROSS REFERENCE TO RELATED APPLICATIONS

This application is the National Stage of PCT/CH2015/000039 filed on Mar. 12, 2015, which claims priority under 35 U.S.C. § 119 of European Application No. 14405023.4 filed on Mar. 13, 2014, the disclosures of which are incorporated by reference. The international application under PCT article 21(2) was not published in English.

BACKGROUND OF THE INVENTION

1. Field of the Invention

The present invention relates to a method for cleaning and/or disinfecting a milk-carrying system of a coffee machine, and a coffee machine for implementing the method.

2. The Prior Art

From the prior art coffee machines, in particular fully automatic coffee machines, are known which are suitable for preparing coffee mix drinks. Coffee mix drinks of this type, for example cappuccino, latte macchiato and suchlike, include a greater or lesser proportion of milk.

In order to improve operating convenience it has for some time been usual practice to provide such coffee machines with milk preparation devices which heat supplied milk or mix it with steam and/or air to achieve a foaming effect. For this, the milk is provided in a separate, partially cooled container and supplied via a milk delivery line, for example a milk pipeline, to a milk inlet of the milk preparation system.

The milk preparation device also has fluid inlet and an air inlet. The air inlet is ventilated, i.e. connected to the ambient atmosphere, while the fluid inlet is supplied with a fluid, for example, steam, for conveying and/or warming the milk. Through the Venturi effect the milk is drawn out of the milk storage container, possibly mixed with the steam/air and dispensed at a milk outlet of the milk preparation device.

As milk generally contains a large number of bacteria and spoils relatively quickly, in the conventional systems it is envisaged that flushing after every milk delivery and at least once daily cleaning and/or disinfection, with a germ-killing cleaning agent for example, is carried out. Such cleaning processes are relatively complicated for an operator. During such a cleaning/disinfecting process the user has to perform procedures on the coffee machine several times.

Largely automated cleaning processes for milk-carrying systems in coffee machines are also known. Such automated cleaning and/or disinfecting processes in accordance with the prior art have the drawback that the milk-carrying system cannot be completely cleaned. Additionally a loop is often provided for the cleaning agent, i.e. the same cleaning agent, already contaminated with milk residues after a first cleaning process, is repeatedly conveyed through the milk fluid pathway in subsequent cleaning processes and thus over time becomes more and more contaminated (with an increasing number of successive cleaning processes).

Known from DE 20 2010 010 509 U1 is a cleaning unit for a coffee machine which has a milk-carrying system. Here a permanently installed dispensing and cleaning unit is provided which makes such a coffee machine larger and increases the space required for it. As switching from a milk pathway to a cleaning agent pathway is envisaged, as of the switch-over valve, in the direction of the milk supply, i.e. in the direction of the milk container no complete cleaning and rinsing through of the milk-carrying system is possible.

Known from EP 1 872 698 B1 is a flushing process for the milk-carrying system of a hot drinks machine. In this, water for rinsing is conveyed through the air supply tube of the milk foaming device. In doing so only flushing through with hot water takes place, i.e. no cleaning agent is added. The actual supply pipeline for the milk is not flushed, but disposal of the milk supply pipeline at certain time intervals is envisaged.

From EP 1 656 863 B1 a special embodiment of the milk-steam mixer of a milk preparation device is known. For flushing the mixer the addition of a cleaning fluid is envisaged. Complete flushing of the milk-carrying system, i.e. including the supply tubes, is thereby not possible.

Known from EP 2 363 051 A1 is a fully automatic coffee machine with a so-called milk module with which foamed milk can be produced. In turn, for cleaning the fully automatic coffee machine has a separate cleaning agent reservoir, which increases the space requirement. In the cleaning pathway a non-return valve is provided for separating the milk storage container including a section of its supply line. Complete rinsing of the entire milk-carrying system is not possible with this.

From EP 2 277 419 B1 a drinks machine is known in which a milk supply line is integrated in a milk container for joint cleaning. The milk container, including the milk supply line, must be externally cleaned, i.e. disinfection or cleaning of the entire milk-carrying system in situ is not possible, which increases the operating effort.

SUMMARY OF THE INVENTION

It is the aim of the present invention to set out a method of cleaning and/or disinfecting a milk-carrying system of a coffee machine for producing coffee mix drinks which in a simple manner allows the entire milk-carrying system to be cleaned and/or disinfected. A further aim of the present invention is to propose a coffee machine for producing coffee mix drinks which has a milk carrying system that can be completely cleaned and/or disinfected in a simple manner.

This is achieved through a method with the features described herein as well as a coffee machine with the features described herein.

According to the inventive method for cleaning and/or disinfecting a milk-carrying system (90) of a coffee machine for producing coffee mix drinks, the milk-carrying system comprises the following:

a milk preparation device, with a milk outlet as well as a fluid inlet, an air inlet and a milk inlet, which is designed for conveying milk from the milk inlet to the milk outlet by utilising the Venturi effect; and a milk delivery line, which at a first end is connected to the milk inlet and at another end can be optionally connected to a milk container in such a way that a fluidic connection between the milk inlet and the milk outlet is produced through the milk delivery line.

The method according to the invention has the following preparatory process steps:

detaching the milk delivery line from the milk container and connecting the milk delivery line to a first container, which contains an active cleaning and/or disinfecting substance, in such a way that for the active cleaning and/or disinfecting substance a fluidic connection is produced between the milk inlet and the first container; and positioning of a second container underneath the milk outlet.

The method then comprises the following process steps in this sequence:

delivery of fluid, preferably of steam, to the fluid inlet in order to convey the active cleaning and/or disinfecting substance through the milk delivery line and the milk outlet into the second container in order to thereby clean and/or disinfect the milk-carrying system; and delivery of water to the air inlet and closing of the fluid inlet in order to convey water through the milk inlet into the first container and to convey water through the milk outlet into the second container, in order to thereby flush the milk-carrying system.

The special advantage of the method according to the invention lies in the fact that with only minimal user interaction the entire milk-carrying system, i.e. the entire milk preparation device including the milk delivery lines, in particular a milk pipeline or suchlike, can be simply and completely flushed with an appropriate fluid which has a cleaning and/or disinfecting action. Though the separation into a first and second container, between which there is no exchange connection, the cleaning and/or disinfecting fluid is not conveyed through the milk preparation device and the further milk-carrying system in the form of a loop. Instead, contaminated cleaning and disinfecting fluid is collected in the second container and the clear cleaning and/or disinfecting fluid is thus clearly separated from the contaminated cleaning and/or disinfecting fluid. Through this the cleaning and disinfecting effect is noticeably improved, and the same time the entire system which carries the milk is effectively cleaned.

The cleaning and/or disinfecting fluid, i.e. the ready-mixed active cleaning and/or disinfecting substance in drawn in by means of the Venturi effect in a first process step in which fluid and preferably steam are conveyed to the fluid inlet. The active cleaning and/or disinfecting substance is thus drawn in by the fluid flow, preferably by the steam flow, from the first container through the milk delivery line and conveyed through the milk outlet to clean the system in this way. In the second process step water is then conveyed to the air inlet and (at the same time or previously) the fluid inlet is closed, flushing water (generally drinking water) is conveyed into the milk preparation device and is distributed there. Through this, both the milk outlet and the milk delivery line are flushed and freed of the active cleaning and/or disinfecting substance.

Subsequent to carrying out the method according to the invention the milk-carrying system is ready for operation again in that through renewed connection of the milk delivery line to the milk container (e.g. through simply reconnecting the milk delivery line from the first container to the milk container) appropriate milk preparation can again take place.

In one form of embodiment of the method according to the invention it is envisaged that after the process step of supplying water to the air inlet and closing the fluid inlet, i.e. after the process step of flushing, the method also comprises the process step of supplying steam to the air inlet, wherein steam is preferably supplied to the air inlet in bursts, and whereafter the fluid inlet is closed in order to drive the water out of the milk delivery line and the milk outlet.

Through such a burst of steam after ending of the flushing procedure, residual flushing water can be reliably driven out of the entire milk-carrying system and a subsequent supply of milk with preparation in the milk-carrying system can take place without possible undesirable dilution of the milk with water.

According to a further aspect of the invention it is envisaged that before the first process step, i.e. before the process step of delivering fluid, the method also comprises the process step according to which water, preferably warm water (e.g. with a temperature of 20-40° C.) is supplied to the first container and preferably automatically supplied to the first container, in order to activate the active cleaning and/or disinfecting substance.

This is particularly of advantage if cleaning and/or disinfection is to take place by means of a cleaning concentrate or a cleaner in tablet form which initially has to be made ready for use ("activated") by appropriate dilution. If such dilution takes place automatically through the supply of water, the process can be noticeably simplified and user convenience improved.

According to a further aspect of the invention it is envisaged that the first container and the second container are nested in each other and preferably integrally designed.

In other words, the second container is preferably arranged inside the first container, but is not in direct fluidic connection therewith. For example it can be envisaged that the container is configured as an integral container with several chambers, wherein one container chamber forms the first container and a further container chamber forms the second container. Partition walls are incorporated in the container making it possible to separate the individual container chambers from each other. By providing a separate cleaning container, which is particularly simple to use, the effort of an operator can be further reduced and the method according to the invention simply and reliably carried out.

It is possible to provide the container with a shape matched to the relevant coffee machine and also possibly with a positioning aid so that it is prevented that the second container (or the second container chamber) is incorrectly positioned and is not located under the milk outlet.

It is evident that the second container is open at the top so that with corresponding positioning of the second container under the milk outlet the active cleaning substance and/or flushing water can flow unhindered into this second container. For the sake of simplicity the first container is also open at the top to allow simple filling of the active cleaning and/or disinfecting substance and also, if automatic dilution (activation) of the active cleaning and/or disinfecting substance is envisaged, to make simple automation of this process possible.

According to a further aspect of the invention it is envisaged that at least after implementing the preparatory process steps the method is carried out automatically.

In order to avoid the discussed problem (known from the prior art) of the entire milk-carrying system not being cleaned/disinfected, in the preparatory step at least a manual separation of the milk delivery line from the milk container and connection of the milk delivery line to the first container, e.g. connection of the milk delivery line to a corresponding connection of the first container, is envisaged. However, while afterwards the actual cleaning/disinfecting procedure and flushing procedure is carried out automatically according to this aspect of the invention, user interaction is reduced to what is necessary and the cleaning and/or disinfecting process is simplified. At the same time complete cleaning and/or disinfecting as well as the associated flushing of the entire milk-carrying system is possible.

According to a further aspect of the invention it is envisaged that a switchover valve is provided which through being controlled can assume at least the following position settings:
- connection of a fluid-conveying device, preferably a pump-heating device combination connected to a water supply, to the fluid inlet; and
- connection of the fluid-conveying device to the air inlet and closure of the fluid inlet.

Here, in order to carry out the process step in which fluid is delivered to the fluid inlet and the air inlet is ventilated, the switch-over valve is automatically brought into the former position whereupon the fluid-conveying device is connected to the fluid inlet.

In order to then carry out the process step of flushing, i.e. the process step according to which water is conveyed to the air inlet and the fluid inlet is closed, the switch-over valve is automatically brought into the latter position, i.e. the position in which the fluid-conveying device is connected to the air inlet and the fluid inlet is closed.

By way of such a switch-over valve, which can automatically be brought into various positions it is possible to automatically implement the method according to the invention in a simple manner.

According to another aspect of the invention, when using such a switch-over valve it can be envisaged that the switch-over valve also has the following position setting:
- connection of the fluid-conveying device to a water outlet opening into the first container.

Here it is envisaged that in order to carry out the process stop in which water is supplied to the fist container to activate the active cleaning and/disinfecting substance, the switch-over valve is automatically brought into said position in which the fluid-conveying device is connected with a water outlet opening into the first container.

If the first container is filled with an active cleaning and/or disinfecting substance to be activated, for example a cleaning concentrate or a cleaning tablet, through a switch-over valve with such an additional setting the process step of activating the active cleaning and/or disinfecting substance can be achieved.

According to a further aspect of the present invention, a coffee machine for producing coffee mix drinks is provided which has a milk-carrying system which in turn comprises the following:
- a milk preparation device, with a milk outlet and a fluid inlet, an air inlet and a milk inlet, which is designed for conveying milk from the milk inlet to the milk outlet utilising the Venturi effect, and
- a milk delivery line which at one end is connected to the milk inlet and which at another end can optionally be connected with a milk container in such a way that a fluidic connection between the milk inlet and the milk container is produced through the milk delivery line.

The coffee machine is configured to automatically carry out the above-described method of cleaning and/or disinfecting the milk-carrying system.

Accordingly the coffee machine also comprises: a control device; a fluid-conveying device, which is designed to supply—controlled by the control device—a fluid in the form of water or steam to the milk preparation device; a first container which contains an active cleaning and/or disinfecting substance; and second container arranged or placeable underneath the milk outlet.

The fluid-conveying device is also connected to the milk preparation device in such a way that, controlled by the control device, optionally a fluidic connection between the fluid-conveying device and the fluid inlet or a fluidic connection between the fluid-conveying device and the air inlet can be established.

The milk delivery line is also designed in such a way that the milk delivery line can be detached from the milk container and connected to the first container in such a way that for the active cleaning and/or disinfecting substance a fluidic connection between the milk inlet and the first container is established.

The control device is designed to make the fluid-conveying device supply a fluid, preferably steam, to the fluid inlet in order to convey the active cleaning and/or disinfecting substance from the first container through the milk delivery line and the milk outlet to the second container and to thereby clean the milk-carrying system.

The control device is also designed to make the fluid-conveying device supply water to the air inlet in order to convey water through the milk delivery line into the first container and to convey water through the milk outlet into the second container and thus flush the milk-carrying system.

One form of embodiment of the coffee machine is designed in such a way that the fluid-conveying device is connected to the milk preparation device via at least one switch-over valve controlled by the control device, and through being controlled by the control device the at least one switch-over valve can be optionally brought into one position in which the fluidic connection between the fluid-conveying device and the fluid inlet is established or into another position in which the fluidic connection in which the fluidic connection between the fluid-conveying device and the air inlet is established. Accordingly, through controlling the switch-over valve a fluid can be simply delivered by means of the fluid-conveying device either into the fluid inlet of the milk preparation device or into the air inlet of the milk preparation device.

Another form of embodiment of the coffee machine is configured so that the fluid-conveying device is connected via several valves controllable via the control device to the milk preparation device in such a way that through controlling the valves either the fluidic connection between the fluid-conveying device and the fluid inlet or the fluidic connection between the fluid-conveying device and the air inlet can be established.

In a further development of the coffee machine this has a water outlet for dispensing water which is arranged in such a way that the first container can be filled with water via the water outlet. In a coffee machine further developed in this way particularly simple automation of the entire cleaning process is possible, wherein depending on the cleaning agent used, particularly simple activation of an active cleaning and/or disinfecting substance through the addition of water is possible.

According to a further aspect of the invention, the coffee machine has a container receptacle for an integral combination container of a first container and a second container. The container receptacle is designed to receive the combination container precisely then when the first container in placed in the opening area of the water outlet (i.e. in such a way that via the water outlet water can be filled into the first container) and when the second container is placed in the opening area of the milk outlet (i.e. in such a way that a cleaning or disinfecting fluid can be conveyed via the milk outlet into the second container).

In other words: through appropriate shaping or suchlike the coffee machine has a container receptacle, adapted to the integral combination container, which prevents an operator incorrectly placing the integral combination container under the outlet. In particular, for this a positioning aid can also be provided on the container, which ensures particularly secure use.

The coffee machine can also be equipped with a sensor device which is designed to recognise whether the integral combination container has been received by the container receptacle and is at a position which ensures that water can be filled via the water outlet into the first container and/or a cleaning and/or disinfecting fluid can be conveyed from the milk preparation device via the milk outlet into the second container. Such a sensor device allows automatic recognition of the combination container and automatic verification of whether the combination container is correctly positioned in order to be able to carry out cleaning and/or disinfection of the milk-carrying system correctly (as envisaged). Incorrect operation of the coffee machine during the implementation of the described method of cleaning and/or disinfecting the milk-carrying system (e.g. the unforeseen removal by an operator of the combination container while implementing the described method of cleaning and/or disinfecting the milk-carrying system) can thus be automatically detected by the sensor device. For example, the coffee machine can be designed so that the implementation of the described method of cleaning and/or disinfecting the milk-carrying system can be immediately stopped or prevented as soon as the sensor detects an incorrect positioning of the combination container.

BRIEF DESCRIPTION OF THE DRAWINGS

An embodiment of a coffee machine for implementing the method according to the invention will be described below with the aid of the drawings.

In these.

DETAILED DESCRIPTION OF THE PREFERRED EMBODIMENTS

Figure 1:
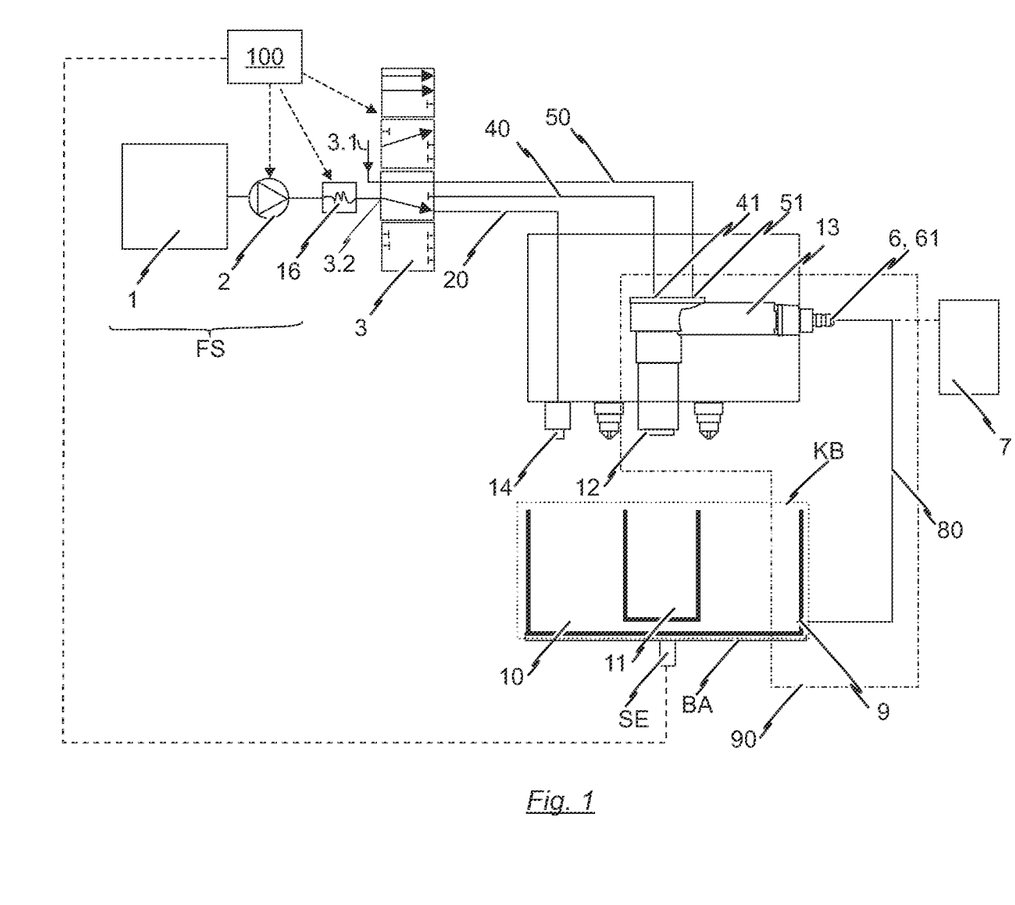
FIG. 1: shows a schematic view of components of a coffee machine, including a milk preparation device with an automatically controllable switch-over valve in a position suitable for mixing.

FIG. 1 shows a schematic view of some components of a not fully illustrated coffee machine for preparing coffee mix drinks according to one form of embodiment of implementing the method according to the invention.

Centrally a milk preparation device 13 is provided which on the right-hand side in the view in FIG. 1 has a line connection 6 for a milk delivery line 80, wherein at the same time the line connection 6 acts as the milk inlet 61 into the milk preparation device 13. The milk preparation device 13 also has a fluid inlet 41 and an air inlet 51 which are connected to a fluid delivery line 40 and an air supply line 50 respectively. On the outlet side the milk preparation device 13 has a milk outlet 12.

In the present example the milk delivery line 80 has two ends wherein at one of these ends the milk delivery line 80 is connected to the line connection 6. At the other end the milk delivery line 80 is connected to a milk container 7 which can be cooled and contains the milk to be prepared.

This connection to the milk container 7 is detachable, i.e. the milk delivery line 80 which is generally in the form of a tube, can be pulled off a corresponding connection of the milk container 7. However, in the connected state, which is shown by the broken line in FIG. 1, during normal operation of the coffee machine when milk is being supplied, i.e. when preparing milk in the milk preparation device 13, at its fluid inlet 41 the milk preparation device 13 can be supplied with steam so that the steam flows through the milk preparation device 13. The aforesaid "connection" of the milk delivery line 80 to the milk container 7 has the purpose of establishing a fluidic connection between the milk inlet 61 and the milk container 7 through the milk delivery line 80. In order to establish a fluidic connection between the milk inlet 61 and the milk container through the milk supply line 80 and thus allow the delivery of milk from the milk container 7 to the milk inlet 61, the milk delivery line 80 does not necessarily have to be physically connected to the milk container 7 and, for example, not necessarily mounted at one end on a connection of the milk container 7: alternatively it is also possible to arrange one end of the milk delivery line 80 in such a way that it is accessible for the milk present in the milk container 7. For example, it would be possible to arrange an end section of the milk delivery line 80 in such a way that at least over part of its length it is immersed in the milk container 7 and in this way is accessible for the milk present in the milk container 7. There, in this context "connecting the milk delivery line 80 to the milk container 7" should be taken to mean in general terms that a fluidic connection of the milk delivery line 80 to the milk container 7 is established and accordingly a fluid present in the milk container 7 can access the milk delivery line 80. Accordingly, in this context "detaching the milk delivery line 80 from the milk container 7" can be taken to mean that the milk delivery line 80 is brought into a state in which there is no fluidic connection between the milk delivery line 80 and the milk container 7 and, accordingly, a fluid present in the milk container 7 can have no access to the milk deliver line 80.

The milk preparation device 13 is configured in such a way that as steam flows through it, a negative pressure is produced in the milk preparation device 13 through the Venturi effect causing milk to be drawn from the milk container 7 through the milk delivery line 80 at the milk inlet 61 of the milk preparation device 13, mixed with the steam and thereby heated. If the air inlet 51 is ventilated, i.e. connected to the ambient atmosphere, in the milk preparation device 13 the milk can also be mixed with air in addition to the steam and thereby be "frothed up" into a milk foam. The milk heated up by the steam in this way or milk foam produced in this way is finally dispensed from the milk preparation device 13 at the milk outlet 12.

To implement the cleaning process according to the invention, in the shown form of embodiment it is envisaged that the fluid delivery line 40 as well as the air supply line 50 are connected to a switch-over valve 3 which on the inlet side has a first inlet 3.1, which is connected to the ambient atmosphere and thus (controllable with the aid of the switch-over valve 3) allows the supply of air into the air supply line 50, as well as a second inlet 3.2, which is connected to a fluid-conveying system FS (hereinafter also called "fluid-conveying device FS"). In the shown embodiment the fluid-conveying system FS (or the "fluid-conveying device FS") is formed by a water tank 1, a pump 2 connected thereto as well as a downstream heating device 16. By way of this fluid-conveying system FS cold, warm or hot water or also steam can optionally be delivered to the second inlet 3.2 of the switch-over valve 3.

In FIG. 1 the switch-over valve 3 is in a position in which it closes the fluid delivery line 40 to the milk preparation device 13. The air supply line 50 of the milk preparation device 13 is connected to the ambient atmosphere via the switch-over valve 3.

A further outlet of the switch-over valve 3 is connected via a water delivery line 20 to a water outlet 14 of the coffee machine, which in the shown embodiment is arranged in a close distance next to the milk outlet 12 of the milk preparation device 13.

Arranged below the milk outlet 12 of the milk preparation device 13 and underneath the water outlet 14 is a combined container KB (hereinafter also "combination container KB" or also "container KB"), which has a first outer container 10 as well as a second inner container 11. As indicated in FIGS. 1-4, the coffee machine comprises a container receptacle BA for the combined container KB. This container receptacle BA is designed so that when accommodated by the container receptacle BA, the combined container KB is each case arranged in a predetermined position relative to the milk preparation device 13. The first container 10 and the second container 11 are open at the top, but are otherwise not fluidically connected to each other. In the shown embodiment the combined container KB, comprising a first container 10 and second container 11, is provided with a (not shown) positioning aid so that an operator will always arrange container KB relative to the container receptacle BA as shown in FIG. 1, namely with the milk outlet 12 directly above the second container 11 and the water outlet 14 immediately above the first container 10.

To initiate the cleaning/disinfection process, an operator detaches the milk delivery line 80 from the milk container 7 and connects it to a line connection 9 formed on the first container 10 and is in fluidic connection therewith. In the following it is assumed that the first container 10 contains an active cleaning and/or disinfecting substance (not shown in FIGS. 1-4).

The purpose of the aforementioned "connection" of the milk delivery line 80 to the line connection 9 is to establish a fluidic connection between the milk inlet 61 and the container 10 through the milk delivery line 80. In order to establish a fluidic connection between the milk inlet 61 and the container 10 through the milk delivery line 80 and thus permit the supply of the active cleaning and/or disinfecting substance from the container 10 to the milk inlet 61, the milk delivery line does not necessarily have to be physically connected to the container 10 and, for example, not necessarily be connected at one end to the line connection 9 of the container 10: alternatively it would also be possible to arrange one end of the milk delivery line 80 in such way that it is accessible to the active cleaning and/or disinfecting substance present in the container 10. It would, for example, be possible to arrange an end section of the milk delivery line 80 in such a way that at least over part of its length it is immersed in the container 10 and in this way is accessible to the active cleaning and/or disinfecting substance present in the container 10.

In this context "connecting the milk delivery line 80 to the container 10" should be taken to mean in general terms that a fluidic connection of the milk delivery line 80 to the container 10 is established and accordingly a fluid present in the container 10 can access the milk delivery line 80.

In the shown position of the switch-over valve 3, water for activating the active cleaning and/or disinfecting substance is then automatically delivered to the container 10, namely by means of the pump 2 and heating device 16, from the water tank 1 through the switch-over valve 3 to the water outlet 14. During this process the heating device is not switched on, i.e. until the required concentration is reached the container 10 is filled with cold or lukewarm water. If before this procedure the heating device 16 has been heated to a temperature greater than the temperature of the water supplied to the container, the heating device 16 is additionally cooled during this process and the water supplied to the container 10 heated.

Figure 2:
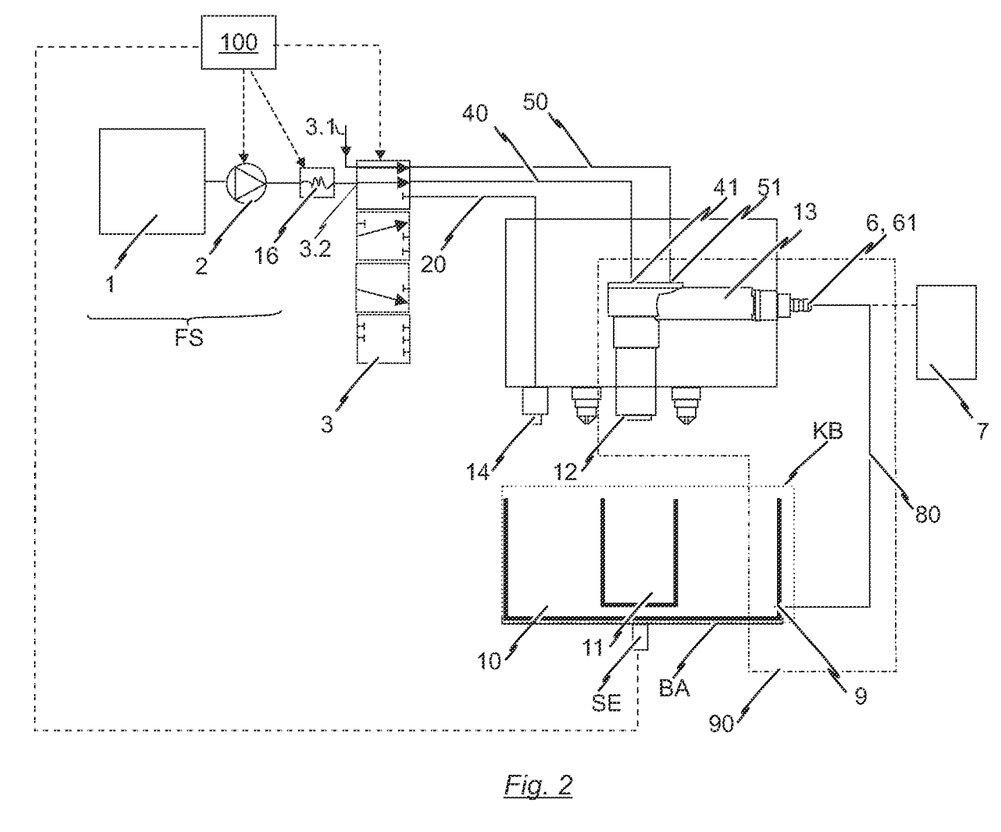
FIG. 2: shows the schematic view in FIG. 1 with the switch-over valve in a position suitable for cleaning and disinfecting.

As soon as the first container 10 has been filled with a predetermined quantity of water, which is such that from the active cleaning and/or disinfecting substance present in the first container 10 and the water contained in the first container 10 a cleaning and/or disinfecting fluid suitable for cleaning and/or disinfecting the milk-carrying system is produced, the switch-over valve 3 is automatically switched to the position shown in FIG. 2. In this position the water outlet 14 is blocked by the switch-over valve 3. While the pump 2 continues to convey water from the water tank 1, the heating device 16 is now switched on so that the fluid-conveying system FS under these conditions delivers steam to the fluid inlet 41 via the switch-over valve 3 and the fluid delivery line 40 (FIG. 2). Due to the Venturi effect, the delivery of steam produces a negative pressure in the milk preparation device 13 so that the cleaning and/or disinfecting fluid is drawn out of the first container 10 via the milk delivery line 80 into the milk inlet 61 of the milk preparation device 13. This cleaning and/or disinfecting fluid contaminated with milk then flows via the milk outlet 12 into the second container.

In the position of the switch-over valve 3 shown in FIG. 2, the air inlet 51 of the milk preparation device 13 is still in connection via the switch-over valve 3/the first inlet 3.1 of the switch-over valve 3 with the ambient atmosphere. In the present example, during the above-described drawing in of the cleaning and disinfecting fluid, this connection with the ambient atmosphere also brings a supply of air into the milk preparation device 13 so that in the milk preparation device 13 the drawn-in cleaning and/or disinfecting fluid is also mixed with air. However, it is pointed out that this supply of air for the above-described cleaning and/or disinfection of the milk preparation device 13 is not necessary. Accordingly, instead of the switch-over valve 3 set out in FIGS. 1-4 it would also be conceivable to use a different valve, which for the purpose of drawing-in the cleaning and/or disinfecting fluid connects the fluid-conveying system FS with the fluid delivery line 40 (as show in FIG. 2), but (alternatively to the situation shown in FIG. 2) tightly closes the air supply line 50 vis-à-vis the first inlet 3.1 of the switch-over valve 3 so that no air can be supplied from the first inlet 3.1 to the air inlet 51.

Figure 3:
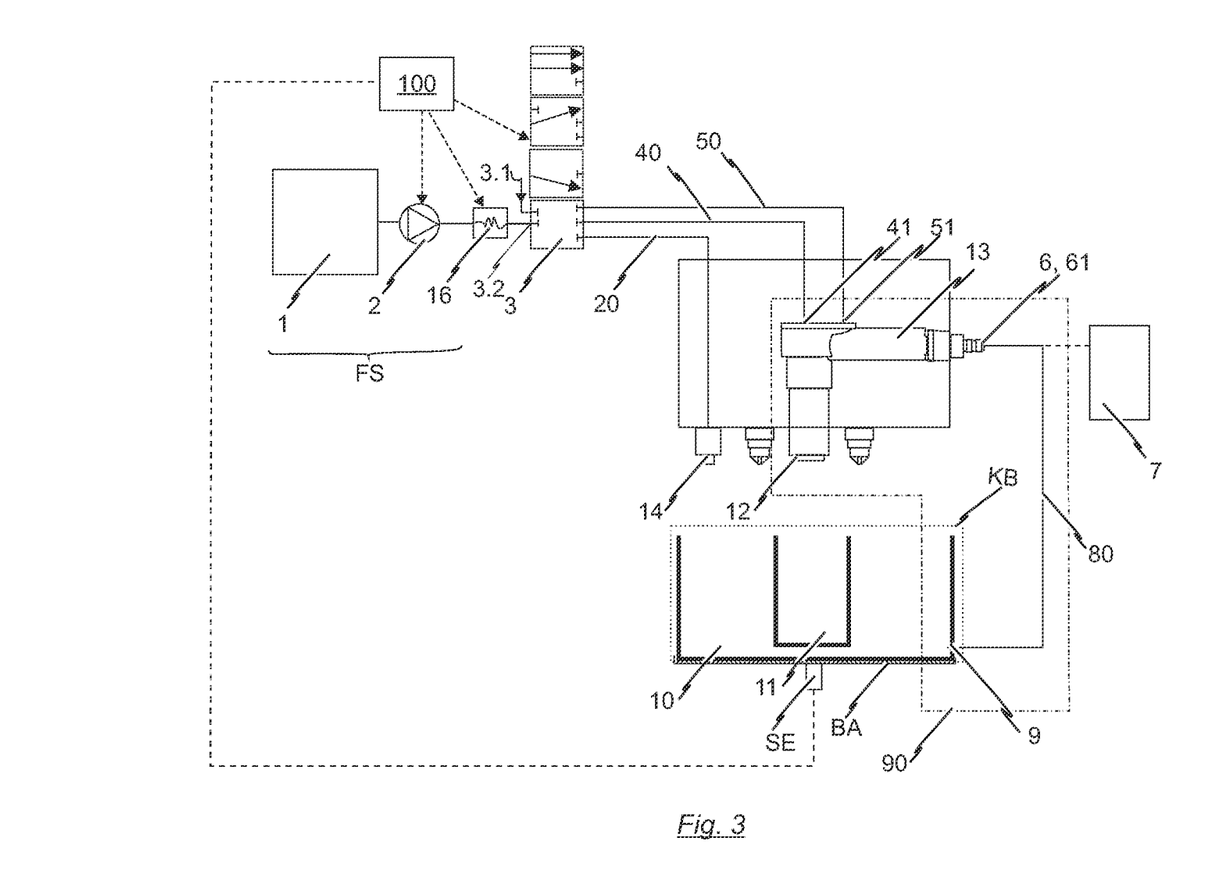
FIG. 3: shows the schematic view in FIGS. 1 and 2 with the switch-over valve in a closed position.

As soon as sufficient cleaning and/or disinfecting fluid has flowed out of the first container 10 through the milk preparation device 13, the pump 2 is stopped and the switch-over valve 3 is brought into a position where it is closed on all sides as shown in FIG. 3.

Figure 4:
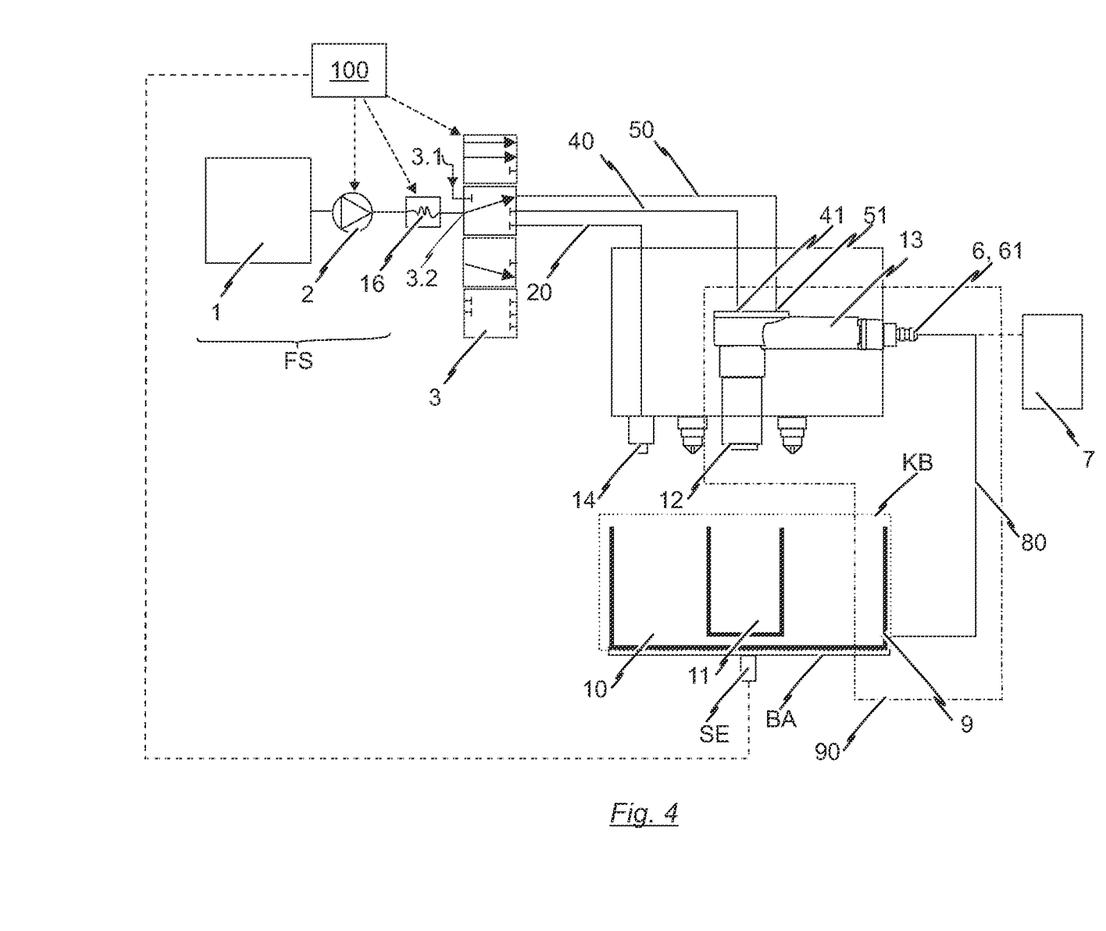
FIG. 4: shows the schematic view in FIGS. 1 to 3 with the switch-over valve in a position suitable for flushing.

The switch-over valve is then brought into the position shown in FIG. 4 in order, subsequent to the above-described cleaning and/or disinfection of the milk-carrying system 90, to make it possible for residues of the cleaning and/or disinfecting fluid possibly present in the milk-carrying system 90 to be removed. Here the fluid inlet 41 of the milk preparation device 13 is no longer connected to the fluid-conveying system FS; rather, via the air supply line 50, the air inlet 51 of the milk preparation device 13 is connected via the switch-over valve 3 to the water tank 1, pump 2 and heating device 16. Clear water (flushing water) is then conveyed from the water tank 1 (preferably drinking water) to the air inlet 51 of the milk preparation device 13 while the fluid inlet 41 is closed via the switch-over valve 3.

The flushing water entering the milk preparation device 13 via the air inlet 51 divides in relation to its flow path and flows both via the milk outlet 12 into the second container 11 and also via the milk delivery line 80 into the first container 10. In doing so the flushing water flushes both the interior of the milk preparation device 13 including the milk outlet 12 as well as the milk delivery line 80 completely. To empty the entire circuit, on completion of the flushing process, through activating the heating device 16 a burst of steam can be conveyed through the milk outlet 12 as well as the milk delivery line 80 so that flushing fluid remaining in this system is largely driven out.

As an alternative to the above procedure, for cleaning and disinfecting the milk-carrying system 90, in the first container 10 it is also possible to provide a cleaning and/or disinfecting substance in the form of a cleaning and/or disinfecting fluid which is already in a ready-to-use state and does not have to be additionally mixed with water. In this case (deviating from the procedure shown in connection with FIG. 1), the supplying of water from the water outlet 14 into the first container 10 at the beginning of the process can be dispensed with. Instead, the cleaning and/or disinfecting fluid provided in the first container 10 is available for cleaning and/or disinfecting the milk-carrying system 90 in its existing form and can be conveyed unchanged—as described in connection with FIG. 2—from the first container 10 via the milk delivery line 80 into the milk preparation device 13.

During the cleaning process the fresh cleaning and/or disinfecting fluid is always separated from the contaminated cleaning and/or disinfecting fluid. This results in reliable cleaning, which, through the connection of the milk delivery line 80 to the line connection 9 of the first container can be carried out in relation to the entire milk-carrying system 90.

As also indicated by FIGS. 1-4, the coffee machine can also be equipped with a sensor device SE which is configured to recognise whether the combined container KB has been accommodated by the container receptacle BA and is located at a predetermined position relative to the milk preparation device 13 in such a way that water can be filled via the water outlet 14 into the first container 10 and/or a cleaning and/or disinfecting fluid can be introduced from the milk preparation device 13 via the milk outlet 12 into the second container 11. For this the sensor device SE can be equipped with sensors suitable for this purpose (e.g. optical, mechanical, magnetic, piezoelectric sensors or suchlike). Accordingly the sensor device SE can be designed to produce signals which indicate whether the combined container KB is located at the predetermined position relative to the milk preparation device 13 as described. The signals produced by the sensor device SE can finally be evaluated by a control device 100 of the coffee machine in order to control the above-described method for cleaning and/or disinfecting the milk-carrying system 90 of the coffee machine. In each of FIGS. 1-4 a broken line indicates a connection between the sensor device SE and the control device 100, said connection serving to transmit the signals produced by the sensor device SE to the control device 100. In connection with this it is assumed that the control device 100 of the coffee machine is designed to control the pump 2, the heating device 16 and the switch-over valve 3 accordingly in order to control the above-described method steps in terms of supplying water, steam or air to the water delivery line 20, the fluid delivery line 40 or the air supply line 50. In FIGS. 1-4 (by means of dashed arrows) connections between the control device 100 and the pump 2, the heating device 16 and the switch-over valve 3 are indicated, said connection serving to transmit the control signals required for controlling the pump 2, the heating device and/or the switch-over valve 3 to the pump 2, the heating device 16 and/or the switch-over valve 3.

Incorrect positioning of the combined container KB can be automatically detected by the control device 100 of the coffee machine by way of the sensor device SE and thus be taken into account when controlling the coffee machine during the implementation of the method for cleaning and/or disinfecting the milk-carrying system 90. For example, the control device 100 can prevent or stop the process for cleaning and/or disinfecting the milk-carrying system 90 as a function of signals of the sensor device SE.

In the examples shown in FIGS. 1-4 a single switch-over valve 3 is provided, which can brought into several positions in order, on the one hand, to be able to establish a fluidic connection between the fluid-conveying system (or the fluid-conveying device) FS and optionally either the water delivery line 20 or the fluid delivery line 40 or the air supply line 50 (via the second inlet 3.2 of the switch-over valve 3), and, on the other hand, to be able to establish a connection between the air supply line 50 and the ambient atmosphere (via the first inlet 3.1 of the switch-over valve 3). It is pointed out that instead of one switch-over valve 3, several separate valves, controllable independently of each other (e.g. by way of the control device 100), can be used in order to control the aforesaid fluidic connections of the water delivery line 20, the fluid delivery line 40 and the air supply line 50 to the fluid-conveying system FS and also the connection of the air supply line 50 with the ambient atmosphere through opening or closing each of the valves.

At this point it is noted that the invention is not restricted to the shown example of embodiment. Modifications thereof are evident to a person skilled in the art.

The invention claimed is:

1. A coffee machine for producing coffee mix drinks, which comprises a milk-carrying system which in turn comprises the following:
   a milk preparation device with a milk outlet as well as a fluid inlet, an air inlet and a milk inlet, which is designed to convey milk from the milk inlet to the milk outlet utilizing the Venturi effect upon a delivery of a fluid to the fluid inlet; and
   a milk delivery line which at one end is connected to the milk inlet and at another end is configured to be optionally connected to a milk container in such a way that a fluidic connection is established between the milk inlet and the milk container through the milk delivery line;
   wherein the coffee machine also comprises:
      a fluid-conveying device which is designed to supply a fluid in the form of water or steam to the milk preparation device,
      a control device configured to control the supply of the fluid to the milk preparation device,
      a first container which contains an active cleaning and/or disinfecting substance, and a second container, arranged or placeable underneath the milk outlet;

wherein the fluid-conveying device is connected to the milk preparation device in such a way that, controlled by the control device, either a first fluidic connection is enabled to be established between the fluid-conveying device and the fluid inlet or a second fluidic connection is enabled to be established between the fluid-conveying device and the air inlet, wherein the fluid-conveying device is designed to supply the fluid to the milk preparation device either via the first fluidic connection between the fluid-conveying device and the fluid inlet or via the second fluidic connection between the fluid-conveying device and the air inlet, wherein the first fluidic connection between the fluid-conveying device and the fluid inlet is configured so that the fluid supplied by the fluid-conveying device to the milk preparation device via the first fluidic connection is enabled to be conveyed through the fluid inlet into the milk preparation device, wherein the second fluidic connection between the fluid-conveying device and the air inlet is configured so that the fluid supplied by the fluid-conveying device to the milk preparation device via the second fluidic connection is enabled to be conveyed through the air inlet into the milk preparation device, wherein the milk delivery line is configured to be detached from the milk container and is configured to be connected to the first container in such a way that for the active cleaning and/or disinfecting substance a fluidic connection between the milk inlet and the first container is established, wherein the control device is designed to cause the fluid-conveying device to supply a fluid to the milk preparation device via the first fluidic connection between the fluid-conveying device and the fluid inlet of the milk preparation device in order to convey the active cleaning and/or disinfecting substance from the first container through the milk delivery line and the milk outlet into the second container and thereby clean the milk-carrying system, and wherein the control device is designed to cause the fluid-conveying device to supply water to the milk preparation device via the second fluidic connection between the fluid-conveying device and the air inlet so that the water being supplied to the milk preparation device via the second fluidic connection is conveyed through the air inlet into the milk preparation device and is distributed in the milk preparation device, enabling a first portion of the water being supplied to the milk preparation device via the second fluidic connection to be conveyed via the milk inlet through the milk delivery line into the first container and enabling a second portion of the water being supplied to the milk preparation device via the second fluidic connection to be conveyed through the milk outlet into the second container and to thereby flush the milk-carrying system.

2. The coffee machine according to claim 1,
wherein the fluid-conveying device is connected by way of a least one switch-over valve, controllable by the control device, to the milk preparation device;
wherein through being controlled by the control device the at least one switch-over valve is configured to optionally be brought into one position in which the fluidic connection between the fluid-conveying device and the fluid inlet is established; and
wherein through being controlled by the control device the at least one switch-over valve is configured to be brought into another position in which the second fluidic connection between the fluid-conveying device and the air inlet is established.

3. The coffee machine according to claim 1, wherein the fluid-conveying device comprises several valves, controllable by the control device, which are connected to the milk preparation device in such a way that through controlling the valves either the first fluidic connection between the fluid-conveying device and the fluid inlet, or the second fluidic connection between the fluid-conveying device and the air inlet is enabled to be established.

4. The coffee machine according to claim 1, wherein the coffee machine also comprises a water outlet for dispensing water, which is arranged in such a way that the first container is configured to be filled with water via the water outlet.

5. The coffee machine according to claim 1, wherein the coffee machine comprises a container receptacle for an integral combination container of the first container and the second container, and
wherein the container receptacle is designed to securely accommodate the combination container such that the first container is arranged beneath an opening of the water outlet and the second container is arranged beneath an opening of the milk outlet.

6. The coffee machine according to claim 5, with a sensor device which is designed to recognize whether the integral combination container has been received by the container receptacle and is in a position that ensures that water can be filled via the water outlet into the first container and/or a cleaning and/or disinfecting fluid can be conveyed from the milk preparation device via the milk outlet into the second container.

7. A method for cleaning and/or disinfecting a milk-carrying system of a coffee machine for producing coffee mix drinks, wherein the coffee machine is the coffee machine according to claim 1,
wherein the method comprises the following preparatory process steps:
detaching the milk delivery line from the milk container and connecting the milk delivery line to the first container; and
positioning the second container underneath the milk outlet,
and wherein the method comprises the following further process steps in this sequence:
further process step one: delivery of fluid to the fluid inlet in order to convey the active cleaning and/or disinfecting substance through the milk delivery line and the milk outlet into the second container in order to thereby clean and/or disinfect the milk-carrying system; and
further process step two: delivery of water to the air inlet and closing of the fluid inlet so that a first portion of the water is conveyed via the milk inlet through the milk delivery line into the first container and a second portion of the water is conveyed through the milk outlet into the second container, so that the milk-carrying system is thereby flushed.

8. The method according to claim 7 wherein the method according to the further process step two comprises the following process step:
delivery of steam to the air inlet and closing of the fluid inlet in order to drive water out of the milk delivery line and the milk outlet.

9. The method according to claim 7 wherein the method before the further process step one comprises the following delivery process step:
 delivery of water into the first container in order to activate the active cleaning and/or disinfecting substance.

10. The method according to claim 7, wherein the first container and the second container are nested in each other.

11. The method according to claim 7, wherein at least after the preparatory process steps the further process steps are implemented automatically.

12. The method according to claim 9, wherein a switch-over valve is provided which through being controlled is enabled to assume at least the following settings:
 position a) connection of a fluid-conveying device to the water inlet; and
 position b) connection of the fluid-conveying device with the air inlet and closure of the fluid inlet,
 wherein for implementing the further process step one the switch-over valve is automatically brought into the position a) and
 wherein for implementing the further process step two the switch-over valve is automatically brought into the position b).

13. The method according to claim 12, wherein the switch-over valve also has the following position:
 position c) connection of the fluid-conveying device with a water outlet opening into the first container
and
 wherein to implement the delivery process step the switch-over valve is automatically brought into the position c).

\* \* \* \* \*